(12) United States Patent
Silver et al.

(10) Patent No.: US 6,356,350 B1
(45) Date of Patent: Mar. 12, 2002

(54) WAVELENGTH MODULATION SPECTROSCOPY WITH MULTIPLE HARMONIC DETECTION

(75) Inventors: Joel A. Silver; David S. Bomse, both of Santa Fe, NM (US)

(73) Assignee: Southwest Sciences Incorporated, Santa Fe, NM (US)

( * ) Notice: Subject to any disclaimer, the term of this patent is extended or adjusted under 35 U.S.C. 154(b) by 0 days.

(21) Appl. No.: 09/364,806

(22) Filed: Jul. 30, 1999

Related U.S. Application Data
(60) Provisional application No. 60/094,872, filed on Jul. 30, 1998.

(51) Int. Cl.[7] .............................................. G01N 21/61
(52) U.S. Cl. ....................................... 356/437; 250/343
(58) Field of Search ................................. 356/437, 438, 356/439; 250/343

(56) References Cited

U.S. PATENT DOCUMENTS

| | | | |
|---|---|---|---|
| 4,468,773 A | | 8/1984 | Seaton |
| 4,990,775 A | | 2/1991 | Rockwood |
| 5,026,991 A | | 6/1991 | Goldstein et al. |
| 5,047,639 A | * | 9/1991 | Wong ........................ 356/436 |
| 5,068,864 A | | 11/1991 | Javan |
| 5,202,570 A | * | 4/1993 | Tanaka et al. .............. 250/343 |
| 5,267,019 A | | 11/1993 | Whittaker |
| 5,448,071 A | | 9/1995 | McCaul |
| 5,498,875 A | | 3/1996 | Obremski et al. |
| 5,636,035 A | | 6/1997 | Whittaker et al. |
| 5,637,872 A | | 6/1997 | Tulip |
| 5,640,245 A | | 6/1997 | Zybin et al. |

OTHER PUBLICATIONS

Bomse, D.S., "Dual–Modulation Laser Line–locking Scheme," *Applied Optics*, vol. 30, No. 21, pp 2922–2924 (Jul. 20, 1991).

Goldstein, N., et al., "Measurement of Molecular Concentrations and Line Parameters Using Line–Locked second Harmonic spectroscopy with an AlGAs Diode Laser," *Applied Optics*,, vol. 31, No. 18, pp 3409–3415 (Jun. 20, 1992).

Silver, J.A., et al., "Frequency–Modulation Spectroscopy for Trace Species Detection: Theory and Comparison Among Experimental Methods," *Applied Optics*, vol. 31, No. 6, pp 707–717 (Feb. 20, 1992).

White, A.D., "Frequency Stabilization of Gas Lasers," *IEE J of Quantum Electronics*, vol. QE–1, No. 8, pp 349–357 (Nov. 1965).

Wilson, G.V.H., "Modulation Broadening of NMR and ESR Line Shapes," *J. Applied Physics*, vol. 34, No. 11, pp 3276–3285 (Nov. 1963).

* cited by examiner

*Primary Examiner*—Richard A. Rosenberger
(74) *Attorney, Agent, or Firm*—Jeffrey D. Myers

(57) ABSTRACT

A method and apparatus for demodulating a plurality of frequency components output from a photodetector in a wavelength modulation spectroscopy system and determining absorption line shapes from the demodulated data. Demodulation is performed with a homodyne demodulator. Line center magnitudes of selected even harmonics of the demodulated output frequency components are measured and the absorption line shape is calculated from the relationship between these magnitudes.

34 Claims, 6 Drawing Sheets

WAVELENGTH MODULATION SPECTROSCOPY WITH MULTIPLE HARMONIC DETECTION

CROSS-REFERENCE TO RELATED APPLICATIONS

This application claims the benefit of the filing of U.S. Provisional Patent Application Ser. No. 60/094,872, entitled Wavelength Modulation Spectroscopy with Multiple Harmonic Detection, filed on Jul. 30, 1998, and the specification thereof is incorporated herein by reference.

GOVERNMENT RIGHTS

The U.S. Government has a paid-up license in this invention and the right in limited circumstances to require the patent owner to license others on reasonable terms as provided for by the terms of Contract No. 50-DKNB-7-90149 awarded by U.S. Department of Commerce.

BACKGROUND OF THE INVENTION

1. Field of the Invention (Technical Field):

The present invention relates to wavelength modulation spectroscopy.

2. Background Art:

Wavelength modulation spectroscopy (WMS) is a form of optical absorption spectroscopy that allows detection of small optical absorbances of gases and, thereby, measurements of gas concentrations. The technique is effective because absorption measurements are shifted from frequencies near DC, where light sources are noisy, to high frequencies where shot-noise-limited absorption measurements are possible. This shift in detection band can improve measurement sensitivity by three to five orders of magnitude.

WMS is usually implemented with continuously tunable lasers such as diode lasers. Typically, the wavelength of the light source is modulated by a small amount about an absorption feature of the target species. The modulation frequency is f. As the light beam propagates through a sample, absorption by the target species converts some of the wavelength modulation into an amplitude modulation (AM) of the light because more light is absorbed at the absorption peak wavelength. When the light impinges onto a photodetector such as a photodiode the output signal from the detector contains AC components at the modulation frequency, f, and its higher harmonics, 2f, 3f, 4f, etc. In conventional usage, one of the AC components is selected for measurement using a phase sensitive detector such as a lock-in amplifier or a mixer. This signal processing step is known as demodulation. Usually a portion of the modulation waveform is used to generate a reference waveform (local oscillator) for the demodulator. The resulting demodulated signal is related to the optical absorbance and to the intensity of the light beam.

Detailed theory describing WMS and the relationships between the absorption lines shape and demodulated line shapes is given by Silver [J. Silver, "Frequency-modulation spectroscopy for trace species detection: theory and comparison among experimental methods," Applied Optics 31, 707–717 (1992)]. In qualitative terms, the waveform produced by slowly stepping the average laser wavelength across an absorption line while demodulating at frequency nf is similar in shape to the nth derivative of the absorption line shape and is referred to as the nf signal or nf spectrum. In the limiting case where the extent (depth) of modulation is much less than the absorption line width, theory predicts that the nf spectrum is directly proportional to the exact nth derivative of the absorption line shape.

The shape of a wavelength modulation spectrum depends strongly on the ratio of the extent of the wavelength modulation to the line width of the absorption feature. Any phenomenon that changes the absorber line width, such as variations in sample pressure or, to a lesser extent, variations in sample temperature, will change the shape and peak intensities of the corresponding wavelength modulation spectrum. Changes in absorber line width can, therefore, introduce error into quantitative applications of WMS particularly where such applications are used to measure species concentrations.

A number of methods exist that can be used to apply wavelength modulation spectra for gas sensing despite changes in the absorber line width; each of these approaches, however, has some limitation. For example, Wilson [G. V. H. Wilson, "Modulation broadening of NMR and ESR line shapes," J. Appl. Phys. 34, 3276–3285 (1963)] shows that the exact shape of a wavelength modulation spectrum can be used to extract the absorber line width and, thereby, calculate the actual optical absorbance and the species concentration. Wilson's method, however, requires WMS measurements that are free of noise and background artifacts (i.e., etalons) in order to obtain accurate line widths, absorbances, and species concentrations. Wilson's numerical inversion methods do not always guarantee convergence and are subject to numerical singularities.

Goldstein et al. patented an improvement to wavelength modulation spectroscopy in which the detector signal at twice the modulation frequency (2f) is monitored while the extent of the wavelength modulation is changed [N. Goldstein, F. Bien, and L. Bernstein, "Gaseous Species Absorption Monitor," U.S. Pat. No. 5,026,991, issued Jun. 25, 1991; N. Goldstein, S. Adler-Golden, J. Lee, and F. Bien, "Measurement of molecular concentrations and line parameters using line-locked second harmonic spectroscopy with an AlGaAs diode laser," Appl. Opt. 31, 3409–3415 (1992)]. The response of the 2f signal as a function of extent of modulation is representative of the shape and width of the absorption line. Goldstein's invention is simple to implement because it requires only a minor modification to standard WMS instrumentation. The most significant limitation of the invention, however, arises because lasers often respond non-linearly to applied modulation waveforms. Both the extent (depth) of modulation and the time dependence of the output wavelength may not track well the changes in the applied modulation signal. Proper implementation of the invention may require careful calibration of the response of each laser or using customized (e.g., non-sinusoidal) modulation waveforms. The nonlinearities are particularly important when relatively large wavelength excursions are needed, such as occur for detecting absorbances from samples at atmospheric or higher pressure.

Species concentrations inferred from wavelength modulation spectra can be corrected by measuring sample temperature and pressure, and using corrections calculated from basic theory or from tabulated calibrations. The computational approach can be slow, however, and requires a significant amount of computing power; tabulating a set of corrections requires a lengthy and tedious calibration. In both cases, the instrument is made more complex and more expensive by adding pressure and temperature sensors.

Other patents discussing related technology but different from the present invention include: U.S. Pat. No. 5,640,245, to Zybin et al., entitled "Spectroscopic Method with Double Modulation;" U.S. Pat. No. 5,636,035, to Whittaker et al., entitled "Method and Apparatus for Dual Modulation Laser Spectroscopy;" U.S. Pat. No. 5,267,019, to Whittaker et al., entitled "Method and Apparatus for Reducing Fringe Interference in Laser Spectroscopy;" U.S. Pat. No. 5,498,875, to Obremsky et al., entitled "Signal Processing for Chemical Analysis of Samples;" U.S. Pat. No. 5,637,872, to Tulip, entitled "Gas Detector;" U.S. Pat. No. 5,448,071 to McCaul et al., entitled "Gas Spectroscopy;" U.S. Pat. No. 5,068,864, to Javan, entitled "Laser Frequency Stabilization;" U.S. Pat. No. 4,990,775, to Rockwood et al., entitled "Resolution Improvement in an Ion Cyclotron Resonance Mass Spectrometer," and U.S. Pat. No. 4,468,773, to Seaton, entitled "Laser Control Apparatus and Method."

U.S. Pat. No. 5,015,848 to Bomse et al., entitled "Mass Spectrometric Apparatus and Method," is related to the field of mass spectrometry, but has no relation to the present invention except for the presence of common inventors, and is included here only for the sake of completeness. Co-pending Application Ser. No. 09/005,356, to Bomse, entitled "Phaseless Wavelength Modulation Spectroscopy," is perhaps most relevant to the present invention and the disclosure therein is incorporated herein by reference. It improves wavelength modulation spectroscopy by extracting information about the line width and line shape of absorption features. The information is in the form of the relative intensities of wavelength modulation spectra acquired at a plurality of demodulated harmonics. This added information can be used to improve the accuracy of gas concentration measurements or to infer physical properties of the gas such as pressure, temperature, and chemical composition.

A key difference between "Phaseless Wavelength Modulation Spectroscopy" and the present invention is that the phaseless method uses one heterodyne demodulation whereas the current invention uses a plurality of homodyne demodulations. In terms of practicality and usefulness, the present invention provides more accurate answers because homodyne demodulations are less noisy than are heterodyne demodulations. The homodyne approach excludes more noise by operating at narrower bandwidth. Also, homodyne demodulations operate at unit duty cycle whereas the heterodyne method—which uses narrow pulses for the local oscillator—acquires demodulated signal only during the pulse "ON" period which may be just a few percent of each demodulation cycle. Regarding apparatus needed to implement the methods, the heterodyne approach requires two modulation frequencies, specified as $\Omega$ and $\delta$, while the current invention needs only one modulation frequency (f). Conversely, the heterodyne approach requires only one demodulation waveform and one demodulator while the current invention requires a plurality of demodulation waveforms (one for each harmonic of f) and is most efficiently implemented using a plurality of demodulators.

The present invention overcomes the limitations of the prior art by demodulating the detector output at a plurality of the harmonic frequencies, not just one, nf. Demodulation at only one frequency, nf, (as conventionally practiced) throws away absorbance information that is available at other harmonics of the modulation frequency. If, instead, the detector output is demodulated at a plurality of frequencies, each frequency being an integer multiple of the wavelength modulation frequency, f, then the resulting signals can be combined to improve the accuracy and precision of the absorbance measurement. The relative magnitudes of the demodulated signals are indicative of the absorber line shape and line width; combining the absorbance data with the line shape information improves the accuracy of the gas concentration measurement over a range of gas pressures, temperatures, and concentrations. The present invention provides a method and apparatus that improves WMS by reducing the measurement uncertainty resulting from such changes. The present invention also permits, under certain circumstances, quantitative determination of spectroscopic absorption line broadening parameters using wavelength modulation spectra.

SUMMARY OF THE INVENTION
(DISCLOSURE OF THE INVENTION)

The present invention is a wavelength modulation spectroscopy system using multiple harmonic detection of the output of the photodetector. A wavelength modulation spectroscopy system has a light source, such as a laser, wavelength modulation means operating at a frequency f, and a photodetector detecting the signal after having passed through the gas, and generating an output with frequency components f, 2f, 3f, . . . nf, where n is an integer greater than one. The present invention improves upon this spectroscopy system by adding a demodulator that demodulates a plurality of the frequency components output by the photodetector. Spectroscopic information is then extracted from the demodulated frequency components to obtain information about the absorption line shape of the gas. In order to extract spectroscopic information, line center magnitudes of the demodulated frequency components are measured at selected even harmonics of the modulation frequency f. A computer or other appropriate device can be used to perform such measurements and measure the line center magnitudes. Then the absorption line shape of the gas can be calculated from the relationship of the line center magnitudes. A computer or various other devices can be used to perform the calculations. Gas concentration, gas temperature, and gas pressure can be determined from the spectroscopic information that is extracted from the demodulated frequency components. Spectroscopic information can be extracted from the full wavelength modulation spectra acquired using demodulation at a plurality of even and/or odd harmonics of the modulation frequency. The system can further be constrained to the absorption line center of a target gas and in this embodiment comprises means for measuring the magnitudes of the demodulated frequency components; means for weighting the magnitudes of the demodulated frequency components at odd harmonics of the modulation frequency, based on known properties of a spectroscopic interference; means for calculating the magnitudes of the frequency components at even harmonics of the modulation frequency, due to an interfering absorption, from the weighted magnitudes; and means for determining the characteristics of the target gas, free of interferences by adjacent absorption lines, from the results of the calculation. Means for perfroming the measurements, weighting, and performing the various calculations can include, but are not limited to, a computer.

In order to perform the demodulation, a plurality of separate demodulators can be used which correspond to the selected frequency components at which demodulation is to be performed. In one embodiment the separate demodulators are each comprised of a local oscillator generating a frequency equal to a separate one of each of the selected frequency components output by the photodetector, and a mixer for performing homodyne demodulation of the frequency component. As an alternative to the first embodiment the plurality of separate demodulators are each comprised of a local oscillator again generating a frequency equal to a separate one of each of the selected frequency components output by the photodetector, and a lock-in amplifier for performing homodyne demodulation of the frequency component.

In a second embodiment the demodulator of the system comprises an analog to digital converter to convert the output of the photodetector into digital data and a computer which performs numerical demodulation of the digital data. This system can further comprise a filter for filtering noise from the demodulated digital data. The computer can perform the numerical demodulation in one of two ways, either by fast Fourier transforms or by vector dot product operations.

In a wavelength modulation spectroscopy method comprising the steps of modulating at a frequency f and generating a photodetector output having frequency components f, 2f, 3f, . . . nf, where n is an integer greater than one, the improved method comprises the step of demodulating a plurality of the frequency components output by the photodetector. The method further adds the step of extracting spectroscopic information from the demodulated frequency components to obtain absorption line shape information. In order to extract the spectroscopic information, line center magnitudes of selected even harmonics of the demodulated frequency components are measured. Then the absorption line shape can be calculated from the relationship of the line center magnitudes. An additional step can be performed wherein gas concentration, gas temperature and gas pressure can be calculated from the spectroscopic information of the demodulated frequency components. The method is also used to determine characteristics of a target gas, free of interferences by adjacent absorption lines, by first constraining the mean modulation wavelength to the absorption line center of a target gas; second measuring the magnitudes of the demodulated frequency components; third weighting the magnitudes of the odd harmonic demodulated frequency components based on known properties of spectroscopic interference; fourth calculating the magnitudes of the even harmonic demodulated frequency components due to an interfering absorption from the weighted magnitude of the odd harmonic demodulated frequency components; and finally determining the target gas characteristics from the calculation step.

The method of demodulating is comprised of demodulating selected frequency components output from the photodetector with a plurality of separate demodulators corresponding with each of the selected frequency components. In order to perform the demodulation, a frequency is generated which is equal to a separate one of each of the selected frequency components using a local oscillator; and then homodyne demodulation is performed on each frequency component with a mixer. Alternatively, demodulating can be accomplished by generating a frequency with the local oscillator, and then performing homodyne demodulation of each frequency component with a lock-in amplifier. Another way of performing the demodulating comprises converting the photodetector output into digital data with an analog to digital converter and then numerically demodulating the digital data with a computer. Noise can then be filtered from the demodulated digital data with a filter. The computer can perform the demodulation either via fast Fourier transforms or vector dot product operations.

A primary object of the present invention is to provide means for improving the accuracy and precision of wavelength modulation spectroscopy absorption measurements.

A primary advantage of the present invention is that absorption line shapes can be determined more accurately.

Another advantage of the present invention is that various gas characteristics can be determined noninvasively.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED EMBODIMENTS

BEST MODES FOR CARRYING OUT THE INVENTION

When the wavelength of a laser is modulated at frequency f, absorption by the target species converts some of the wavelength modulation into amplitude modulation (AM) of the light. The amplitude modulation occurs at the modulation frequency, f, and its integer harmonics, 2f, 3f, 4f, etc. As the light impinges onto a photodetector such as a photodiode, the output signal from the detector contains AC components that are synchronous with these AM frequency components. Typical WMS applications use a phase-sensitive detector such as a mixer or lock-in amplifier to measure the AC intensity at one frequency and thereby generate a signal that is proportional to the optical absorbance. This signal processing step is known as demodulation.

Figure 3:
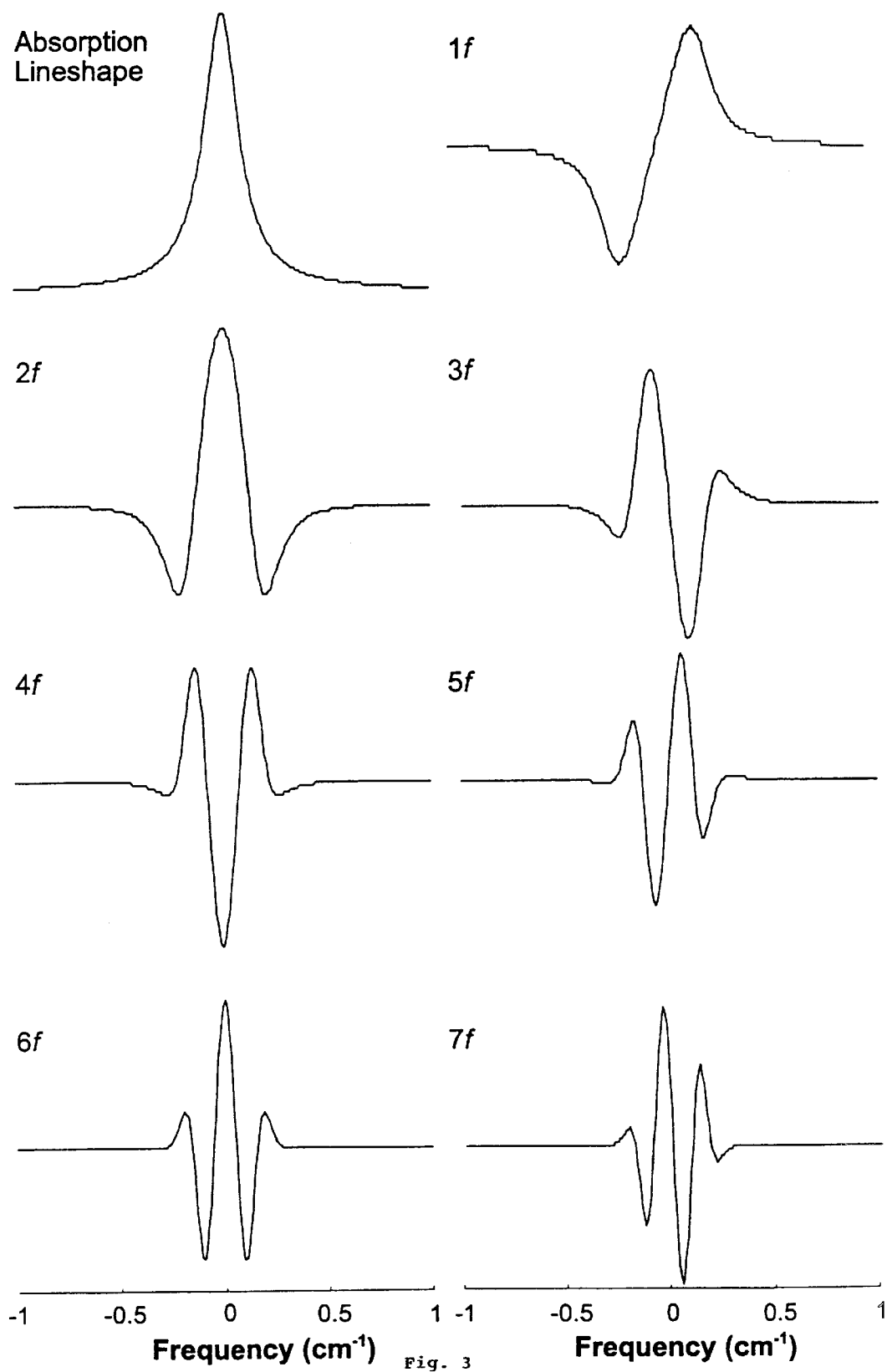
FIG. 3 is a representation of absorption and wavelength modulation line shapes.

One way to visualize the usefulness of multiple harmonic detection is to recognize that the demodulated waveforms are qualitatively similar to the corresponding derivatives of the absorption line. In other words, the 2f waveform obtained by demodulating the detector output at twice the modulation frequency, 2f, is similar in shape to the second derivative of the absorption line. FIG. 3 shows representative shapes of an absorption line and its corresponding harmonic line shapes. Representative absorption and wavelength modulation line shapes are shown for an atmospheric pressure broadened line having a line width of 0.1 cm$^{-1}$. The wavelength modulation line shapes, 1f, 2f, etc., were computed assuming a modulation depth of 2.2 times the absorption line width. Combining the information from demodulation at multiple harmonics is similar to a derivative series expansion of the line shape in the region around the absorption line. Much of the line shape can be obtained from a few, discrete measurements. The spectroscopic information derived from the demodulated frequency components can include the optical absorbance, the absorption line shape, and the absorption line width, from the magnitudes and phases of the demodulated components.

For most WMS applications, in which a tunable laser probes a single, well-resolved absorption line, the functional form of the absorption line shape is well known and the relationships among the relative magnitudes of the demodulated signals are defined by just two parameters: the line width and the extent (depth) of laser wavelength modulation. The depth of wavelength modulation is usually determined during instrument set up or calibration. Therefore, measurement of the signals from two demodulations is sufficient to determine the absorber line width. Additional measurements from additional demodulations can improve overall measurement accuracy.

One important application of wavelength modulation is continuous measurement of the concentration of a selected gas effected by measuring the optical absorbance at a wavelength coincident with the center of an absorption line of the gas. WMS theory predicts that even harmonic demodulated frequency component waveforms (nf for n=2, 4, 6, etc.) show extrema at line center while odd harmonic demodulated frequency component waveforms (nf for n=1, 3, 5, etc.) are zero at line center, FIG. 3. Measurement of the line center magnitudes of a plurality of even harmonic demodulated frequency component signals can provide target gas concentrations independent of substantial variations in the absorption line width.

The general form of an absorption line shape for gases is the Voigt function which is a convolution of a Lorentzian component due to collisional broadening and a Gaussian component due to the distribution of molecular velocities (the Doppler effect). The Voigt line shape absorption cross section as a function of optical frequency, v, is given by, $$\alpha(v-v_0) = \frac{1}{\pi \Delta v_D} \left(\frac{\ln 2}{\pi}\right)^{1/2} \left(\frac{\Delta v_L}{\Delta v_D}\right)(\ln 2)^{1/2} \int_{-\infty}^{\infty} \frac{e^{-t^2} dt}{y^2 + (x-t)^2},$$

where:

$$x = \frac{v - v_0}{\Delta v_D} (\ln 2)^{1/2},$$

$$y = \frac{\Delta v_L}{\Delta v_D} (\ln 2)^{1/2},$$

$v_0$ is the absorption line center frequency, and $\Delta v_D$ and $\Delta v_L$ are the Doppler and Lorentzian line widths, respectively. At line center, $v = v_0$, the absorption cross section becomes:

$$\alpha_0 = \frac{e^{y^2} \text{erfc}(y)}{\sqrt{\pi}},$$

where erfc is the complementary error function. The important line shape information is contained in the Voigt parameter y.

WMS measurements using even harmonic demodulated frequency components are practical because the average (i.e., unmodulated) laser wavelength can be controlled to the absorption line center using line-locking methods that are compatible with wavelength modulation spectroscopy [D. S. Bomse, "Dual Modulation Laser Line Locking Scheme," *Applied Optics* 30, 2922–2924 (1991) and A. D. White, "Frequency stabilization of gas lasers," IEEE *Journal of Quantum Electronics*, QE-1, 349–357 (1965)]. One can also scan slowly the average (i.e., unmodulated) laser wavelength across the entire absorption line while detecting at a plurality of demodulation frequencies and analyze the resulting full WMS line shapes to determine the gas concentration and absorption line width.

Figure 1:
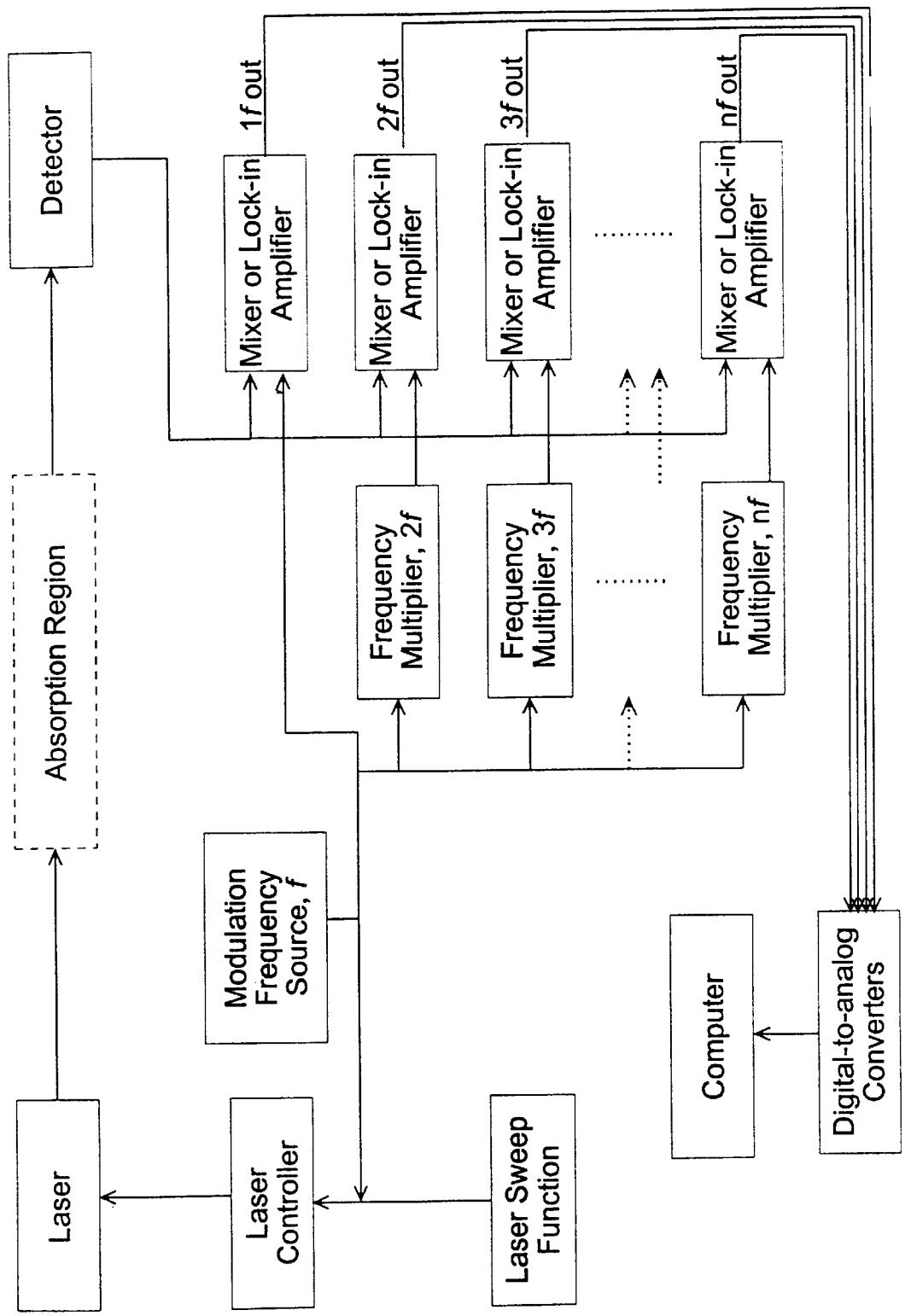
FIG. 1 is a block diagram of a first embodiment of the present invention.

A first implementation of the present invention uses a plurality of demodulators (e.g., mixers or lock-in amplifiers). FIG. 1 shows a schematic diagram of the first embodiment for performing wavelength modulation spectroscopy with multiple harmonic detection. Each demodulator uses a different harmonic of the modulation frequency, f, as its local oscillator (reference) input. This approach allows simultaneous or nearly simultaneous acquisition of a plurality of harmonic spectroscopic waveforms.

Figure 2:
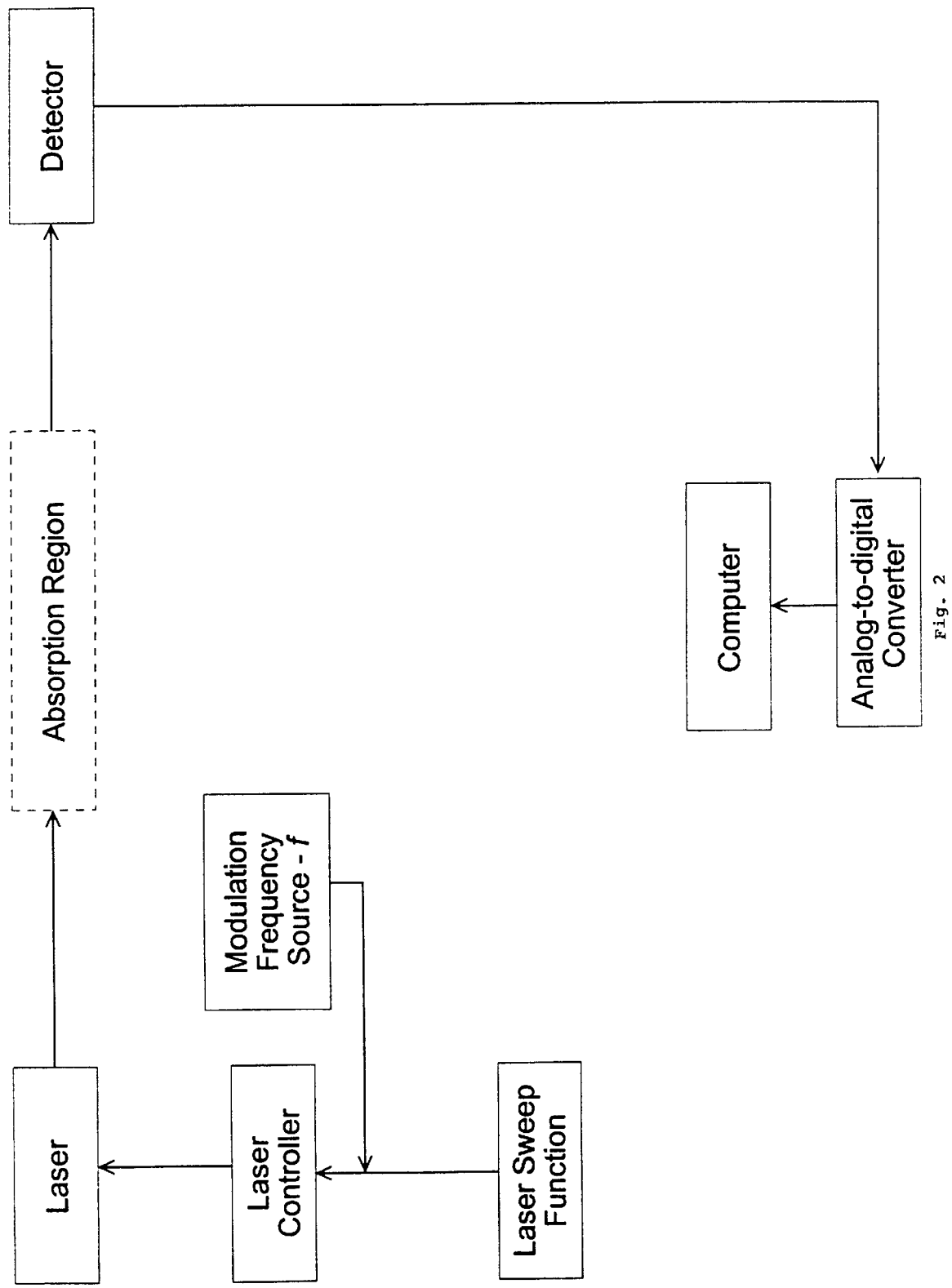
FIG. 2 is a block diagram of a second embodiment of the present invention;.

A second embodiment of the present invention takes advantage of recent developments in digital signal processing (DSP) electronics and is shown in FIG. 2. The detector output is first digitized, then numerical methods are used to demodulate the data stream at multiple harmonics of the modulation frequency. The output from the photodetector is digitized after a minimal amount of analog signal conditioning. The resulting digitized waveform is then demodulated numerically to yield spectroscopic information indicative of, for example, the magnitude, or magnitude and phase, at frequencies corresponding to a plurality of integer harmonics of the modulation frequency, f. One advantage of this DSP approach is that only a single digitizer is required to obtain information at a plurality of demodulated harmonic frequency components. The digital demodulation step may include fast Fourier transform (FFT) of the input data to determine the signal strengths and relative phases at harmonics of the modulation frequency. Digital demodulation may instead include vector multiplication of the digitized data by numeric series representing sine and/or cosine waveforms at one or more harmonics of the modulation frequency. In either case, the highest harmonic detected is roughly half of the ratio of the Nyquist sampling frequency to the modulation frequency. Analog and/or digital filtering prevents introduction of noise, or higher frequencies, (e.g., aliasing) into the demodulated data streams.

Wavelength modulation with multiple harmonic detection may also prove useful for distinguishing absorbances due to overlapping absorption lines and etalons. Three features of WMS are used: that absorption line shapes are well known, that the relative magnitudes of the different demodulated waveforms vary in a predictable way for each absorption line, and that the wavelengths of absorption line centers are nearly constant. The present invention is particularly useful for systems in which all interfering spectroscopic lines are well characterized; mathematical fitting routines need only extract linear combinations of signal intensities from interfering lines having known wavelengths. In special cases, where the average (unmodulated) laser wavelength is constrained to the center of an absorption line of a target gas, signals demodulated using odd harmonics of the modulation frequency are all expected to be zero. Non-zero signals are likely due to spectroscopic interferences. The magnitude of the interference can be measured using selected odd harmonic demodulated frequency components; then the corresponding signals for the even harmonic demodulated frequency components of the interference can be calculated based on the weighted magnitudes of the odd harmonic demodulated frequency components. The selected odd harmonic demodulated frequency components are weighted by amounts representative of the spectroscopic interference, based on known properties of the spectroscopic interference, and allow calculation of the corresponding even harmonic demodulated frequency components due to the interference. These calculated signals for the even harmonic demodulated frequency components can be subtracted from the measured even harmonic demodulated frequency components to yield measurements characteristic of the target gas free of interferences by adjacent absorption lines. Various means can be used for measuring magnitudes and performing the described mathematical operations, and include but are not limited to, computers.

Absorbances due to gases at high pressures and even liquids may be measured using the present invention even though the laser cannot tune across the full absorption line. WMS measurements at or near the line center using multiple harmonic detection should provide sufficient information to determine the optical absorbance.

The prior art method of wavelength modulation spectroscopy wherein typically one harmonic frequency is demodulated operates under the assumption that the absorption line wave shape is not changing. However, changes in, for example, temperature and pressure, change the shape of the absorption line. If it is possible to get information on how the absorption line wave shape is changing from the output demodulated harmonic spectrum, then it might be possible to work in reverse and determine, for example, the temperature and pressure. Because the relative intensities of the demodulated spectra change as the width of the absorption line shape changes, measuring signals demodulated at a plurality of harmonics provides an additional means of calculating the gas concentration. Therefore, if it is possible to understand the mechanisms that change the absorption line wave shape width, then it may also be possible to determine these other properties with non-invasive means. The present invention provides such a means and is potentially a powerful tool in determining gas characteristics in a non-invasive manner.

One embodiment of the invention using commercially available components is as follows: Multiharmonic wavelength modulation spectra of water vapor can be acquired using a near-infrared DFB diode laser, such as a Sensors Unlimited SU1393-DFB-CD-C laser, operating at nominally 1393 nm. The laser temperature and DC current are regulated by an ILX3722 diode laser controller. The laser wavelength is modulated by applying the sine wave output at 10 kHz from a Stanford Research model 830 lock-in amplifier to the AC input on the ILX controller.

Light from the diode laser is collimated using a ThorLabs model C350TM aspheric lens, anti-reflection coated for operation in the 1050 to 1550 nm wavelength region. The collimated beam is directed through a sample region containing an unknown amount of water vapor and is then focused onto a photodetector such as a Fermionics FD1000W InGaAs photodiode. The electronic output from the photodetector is connected to the signal input of the lock-in amplifier and the lock-in amplifier is set to process one harmonic of the 10 kHz modulation frequency. A wavelength modulation spectrum is acquired using a computer to step the (center) wavelength of the diode laser across the water absorption feature at 7181.17 $cm^{-1}$ (1392.53 nm) while recording the demodulated signal from the lock-in amplifier at each wavelength. Typically from 30 to 200 wavelengths steps are used spanning from 3 to 5 full widths of the absorption line.

After one WMS spectrum is acquired, the lock-in amplifier is set to another harmonic of the modulation waveform and an additional WMS spectrum is similarly acquired. Implementation of this embodiment requires that at least two such WMS spectra be acquired under nominally identical sample conditions and at the same modulation depth. This embodiment offers the advantage of using a simple-to-operate commercial lock-in amplifier that both generates the modulation sine wave at a user-selectable frequency and magnitude, and demodulates the detector output at any user-selectable harmonic for demodulation frequencies up to 100 kHz.

The embodiment represented by FIG. 1 allows simultaneous acquisition of wavelength modulation spectra at a plurality of demodulation frequencies. In this case, a separate demodulator and local oscillator (reference waveform) is required for each demodulation and output from the photodetector is distributed among the inputs of each demodulator. The demodulators can be double-balanced mixers such as a Mini-Circuits ZLW-6 which performs at frequencies ranging from 3 kHz to 100 MHz. The frequency multipliers can be constructed from phase-locked-loop integrated circuits such as a Motorola MC74HC4046AN and a digital counter such as a Motorola MC74HC4040AN. The laser modulation waveform can be generated using a commercial function generator such as a Stanford Research model 545 function generator.

In the embodiment represented by FIG. 2, the electronic output from the photodetector is digitized at a rate that is at least a factor of two greater than the largest demodulation frequency of interest and the resulting digital data are demodulated numerically using a computer. One method for numerical demodulation uses a simple vector dot product operation in which the digitized data, configured as a one-dimensional array, form one vector and the other vector is a pseudo-sine wave containing a repeated series such as 0, 1, 0, −1 . . . or a pseudo-cosine wave containing a repeated series such as 1, 0, −1, 0 . . . Different demodulation frequencies can be selected by changing the stride of the demodulation wave form. That is, a pseudo-sine wave defined by the series 0, 1, 0, −1, 0, 1, 0, −1 . . . will extract signals at twice the frequency of a pseudo-sine wave defined by the series 0, 0, 1, 1, 0, 0, −1, −1 . . .

The phase of each demodulation can be changed by combining the dot product obtained using a pseudo-sine wave with the dot product obtained using the corresponding pseudo-cosine wave. Each dot product result corresponds to the average voltage generated by an analog, electronic demodulator for a comparable measurement period or bandwidth.

In an alternative embodiment of FIG. 2, the detector output is digitized at a rate that is at least a factor of two greater than the largest demodulation frequency of interest. However, the numerical demodulation is performed by calculating the fast Fourier transform (FFT) of the digitized data and extracting from the array of transformed data those values which define spectroscopic information, such as the magnitude and phase of the digitized data at each harmonic frequency of interest.

The digital methods described in these embodiments have the advantage of performing multiple demodulations on one data stream. It is relatively straightforward to synchronize a computer-generated modulation waveform with the analog-to-digital conversion of the photodetector output. Continuous, real-time measurements are possible at digitization frequencies up to several hundred kilohertz using commercially available single board computers such as the Innovative Integration SBC32.

Of the two digital approaches, the embodiment which performs demodulations using the vector dot products has the advantage of allowing finer control of the demodulation frequency than does the FFT approach. In contrast, the FFT method may be computationally faster when trying to perform a large number of numerical demodulations. In both cases, better performance may be obtained by windowing the data using a Hamming filter or similar filter.

Of course, many different types of electronic components other than those described here can be used to implement the invention and would be apparent to those skilled in the art. Various means can be used for measuring and extracting spectroscopic information and performing described mathematical operations and include, but are not limited to, computers.

Industrial Applicability:

The invention is further illustrated by the following non-limiting examples.

EXAMPLE 1

Relative WMS Signals for Water Vapor

As an example of the usefulness of the present invention, the relative WMS signals (peak heights) expected at line center for a water vapor absorption peak that would be useful for airborne hygrometry and for trace moisture measurements in industrial processes were calculated. The absorption line is the (303)←(202) transition in the $v_1+v_3$ vibrational band at 7181.1719 $cm^{-1}$ characterized by an absorption line strength at 296 K of $1.80 \times 10^{-21}$ $cm^{-1}$ molecule$^{-1}$, a Doppler line width of $\Delta v_D = .0104$ $cm^{-1}$ at 296 K and a Lorentzian line width given by $\Delta v_L = 0.1031(1-\chi) + 0.4630\chi$ $cm^{-1}$ where $\chi$ is the water vapor mole fraction. Line parameters are reported in well-known references. This transition is particularly useful for trace water measurements because of its large line strength (within an order of magnitude of the largest infrared line strength for water) and because the optical frequency can be reached by commercially available, single frequency, diode lasers operating at room temperature.

Figure 4:
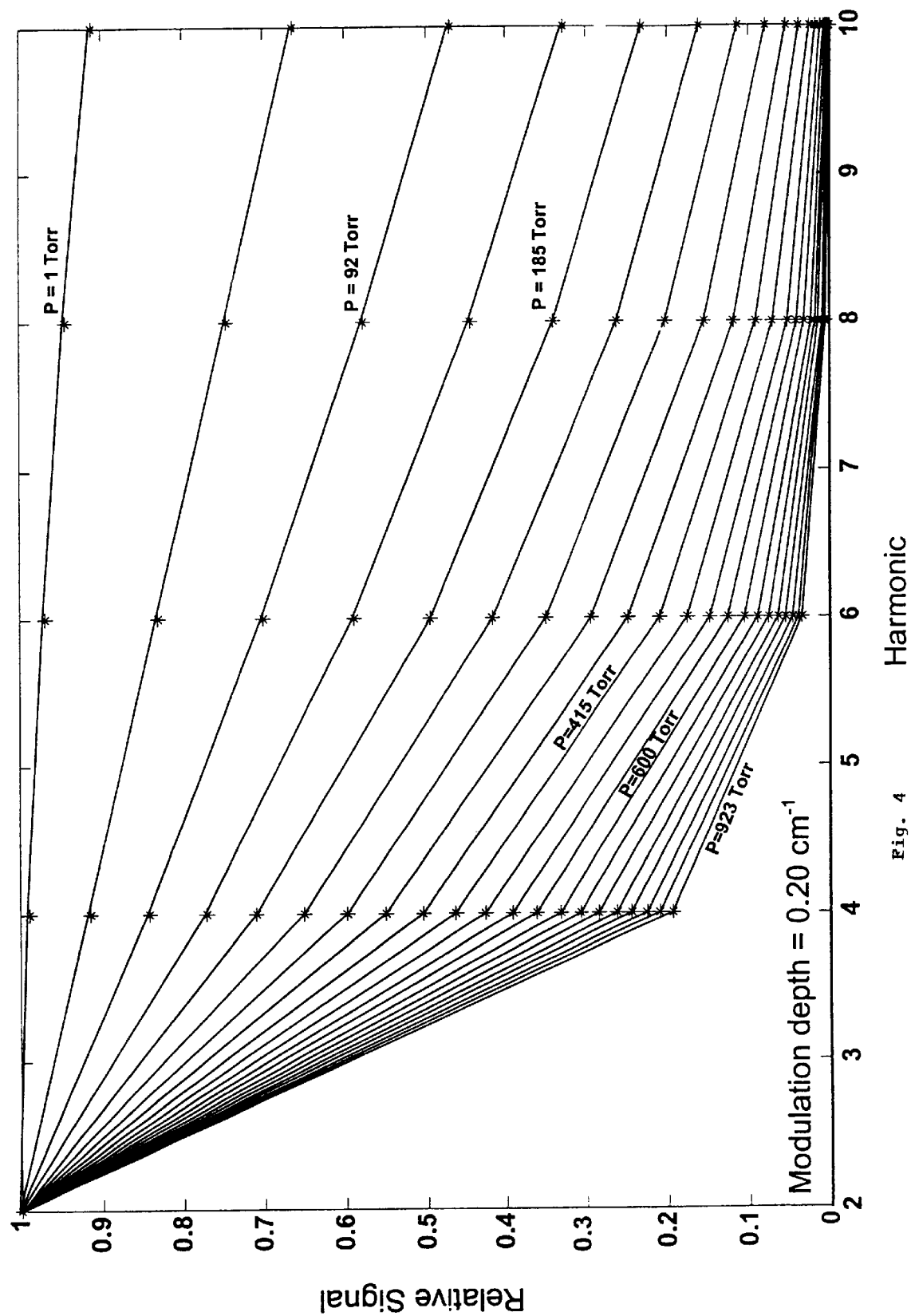
FIG. 4 shows relative intensities of wavelength modulation spectroscopy signals at absorption line center for even harmonic demodulated frequency components at a modulation depth of 0.2 $cm^{-1}$ for a variety of water vapor gas pressures between 1 and 923 torr.

FIG. 4 shows a family of curves indicating WMS relative peak amplitudes at line center for signals demodulated at even harmonics of the modulation frequency at different pressures when the modulation depth is fixed at 0.20 $cm^{-1}$. Relative intensities of WMS signals at absorption line center for even demodulation harmonics, nf (n=2, 4, 6, 8, and 10), for a variety of gas pressures between 1 and 923 torr are shown. Calculations were performed using the method described by Silver and assume T=296 K and $\chi$<<1. There is significant variation among the relative peak magnitudes for pressures up to ~600 torr.

Figure 5:
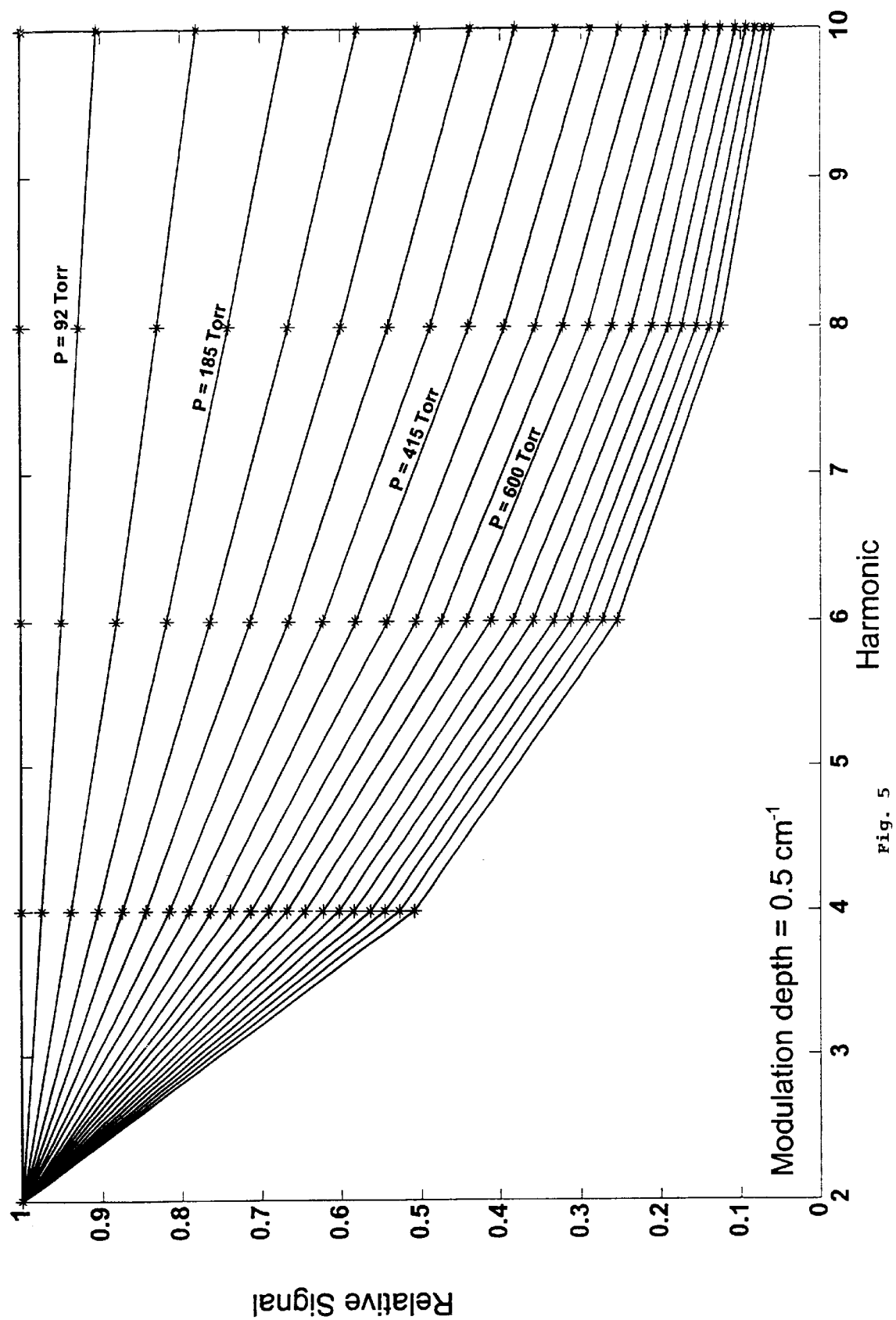
FIG. 5 shows the same information as FIG. 4 at a modulation depth of 0.5 $cm^{-1}$ for a variety of gas pressures between 1 and 1000 torr.

FIG. 5 shows a similar set of curves for a fixed modulation depth of 0.50 $cm^-$. Relative intensities of WMS signals at absorption line center for signals demodulated at even harmonics, nf (n=2, 4, 6, 8, and 10), for a variety of gas pressures between 1 and 1000 torr are shown. In this case, useful line shape data can be obtained for pressures in the range of ~100 torr to 1 atmosphere.

The results presented in FIGS. 4 and 5 imply a unique relationship between the absorption line shape and the relative magnitudes of the even harmonic demodulated WMS signals. For experimental measurements, the observed signal intensities depend on the absorber concentration, gas temperature, and gas pressure. Even in special cases, where the gas pressure and temperature are controlled to predetermined values, WMS detection using multiple harmonic demodulation can improve the accuracy of gas concentration measurements by including more information than is acquired when only one demodulated harmonic is detected.

EXAMPLE 2

Evaluating Multi-Harmonic Data to Retrieve Desired Parameters

Measurement of wavelength modulation data returns a spectrum whose magnitude and shape depend on the spectroscopic parameters of the gas of interest, the modulation depth, the total temperature and pressure, and the gas number density (concentration). This waveform may be expressed, in general, as the integral over the modulation waveform evaluated at the $n^{th}$ harmonic:

$$Sig_n(v) = \frac{2n!}{\pi 2^{1-n} m^n} \int_0^\pi g(v + m\cos\theta) d\theta,$$

where v is the laser wavelength in units of $cm^{-1}$, g(v) is the normalized Voigt line shape function (i.e., integrated area of unity) which is a function of the spectroscopic parameters, temperature T, mass M, and pressure P, and where n is the harmonic of the modulation frequency at which the signal is detected, and m is the modulation depth in $cm^{-1}$ (center to maximum excursion). This signal is then scaled by number density, path length and absorption line strength to provide the absolute absorbance.

The Voigt profile varies as a parameter defined as y, which is the ratio of the Lorentzian (pressure) broadening coefficient $\Delta v_L$ to the 1/e height Doppler broadening coefficient $\Delta v_{1/e}$, $$g(v) = f(v/\Delta v_{1/e}, y),$$

$$\text{where } \Delta v_{1/e} = \frac{3.56 \times 10^{-7}}{\sqrt{\ln 2}} v_0 \sqrt{\frac{T}{M}},$$

$$\Delta v_L = bP,$$

$$\text{and } y = \frac{\Delta v_L}{\Delta v_{1/e}}$$

The line center absorption wavelength is $v_o$. The pressure broadening coefficient b varies with each spectroscopic line and may also be temperature dependent. The desire is to determine either b or P, given the other. This is made possible by finding the value of y which best fits the data.

Therefore the goal in a measurement is to determine the value of y for a given set of experimental parameters. A WMS system with a known modulation depth and temperature was configured and line shapes at each even demodulated harmonic 2,4,6, ... were measured. If the signal intensities are restricted to line center only (which are nonzero for even values of n), the series of curves of the predicted intensity $Sig_n(0)$ for different values of y can be computed. These are shown by the solid curves in FIG. 6, where all curves are normalized to their value at the $2^{nd}$ harmonic ($Sig_2(0)$). It is obvious from the experimental signal ratios at the even demodulated harmonics, that the best value of y should be able to be inferred. Although this is possible from measuring, for example the ratio of n=4/n=2, multiple demodulated harmonics are used instead to improve the accuracy.

Mathematically this can be accomplished in a number of ways. Since each demodulated harmonic requires an independent measurement, the measured value for each n from the corresponding computed signal ratio function of y is interpolated to get the optimal $y_{expt}(n)$. Then by averaging all of these measurements for however many demodulated harmonics there are, the final answer can be obtained. Of course, this final averaging could include weighting to account for better signal/noise levels or other factors.

Figure 6:
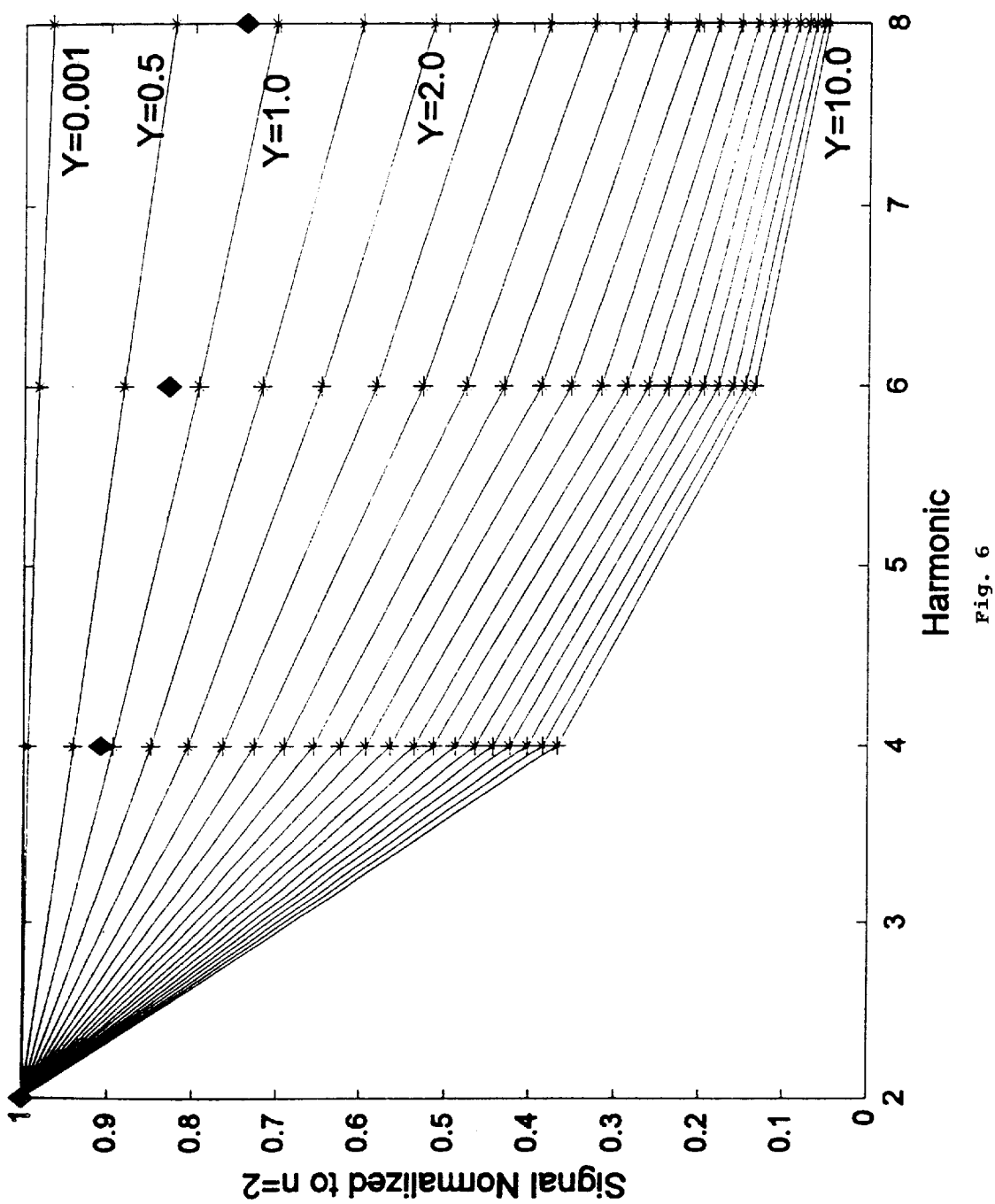
FIG. 6 shows a computed map of harmonic demodulated frequency component peak heights with experimental data shown as diamonds.

For example, suppose the broadening coefficient of a spectroscopic line at known pressure is to be determined. Referring now to FIG. 6, experimental data are shown as diamonds from Table 1. In FIG. 6 the water line is at 7181 $cm^{-1}$, temperature is 296K, and m=0.24$cm^{-1}$. Obviously the correct answer for the experimental value of y lies between 0.5 and 1.0. If the measured values of the signal ratio from the y=0.5 and y=1.0 curves for each n are interpolated, then the numbers shown in Table 1 are obtained. Assuming all are equally weighted, the best (mean) value of the resulting data is $y_{expt}$=0.830.

From this result, using the above equations, and knowing the pressure was 1 atmosphere and $\Delta v_{1/e}$=0.0125 $cm^{-1}$, then the pressure-broadening coefficient b=0.1038 $cm^{-1}$/atm. Conversely, if b was known from experimental data, but not P, then the pressure could be calculated.

TABLE 1

Example of data analysis

| Demodulation Harmonic | Experimental Signal | Signal (y = 0.5) | Signal (y = 1.0) | Interpolated y |
|---|---|---|---|---|
| 4 | 0.91 | 0.9424 | 0.8942 | 0.836 |
| 6 | 0.83 | 0.8837 | 0.7955 | 0.804 |
| 8 | 0.74 | 0.8247 | 0.7040 | 0.851 |

Mean y = 0.830 ± 0.024

In this example, only the WMS peak heights at line center were considered. The entire line shape for each demodulated harmonic frequency component can be used to retrieve the same information, using more complex fitting and interpolation algorithms. This approach can use odd harmonic spectroscopic waveforms as well, since they also have distinctive shapes. The advantage of this latter approach would be that the accuracy is improved, since the results are determined not from just 3 or 4 points of data but from hundreds of data points.

The preceding examples can be repeated with similar success by substituting the generically or specifically described embodiments of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. In a wavelength modulation spectroscopy system comprising modulation means operating at frequency f and a photodetector generating output with a plurality of frequency components at integer harmonics of said operating frequency f, an improvement comprising a demodulator to demodulate a plurality of said frequency components output by said photodetector, including at least two even harmonics.

2. The improved system of claim 1 further comprising means for extracting spectroscopic information from said demodulated frequency components to obtain absorption line shape information.

3. The improved system of claim 2 wherein said means for extracting spectroscopic information comprises means for measuring line center magnitudes of said demodulated frequency components demodulated at selected even harmonics of said operating frequency f.

4. The improved system of claim 3 further comprising means for calculating the absorption line shape from the relationship of said line center magnitudes.

5. The improved system of claim 1 further comprising means for calculating at least one parameter from the group consisting of gas concentration, gas temperature, and gas pressure from spectroscopic information of said demodulated frequency components.

6. The improved system of claim 1 wherein said system is constrained to the absorption line center of a target gas and wherein said system further comprises:
   means for measuring magnitudes of said demodulated frequency components;
   means for weighting said magnitudes of said demodulated frequency components demodulated at odd harmonics of said modulation frequency, f, based on known properties of a spectroscopic interference;
   means for calculating magnitudes of said frequency components at even harmonics of said modulation frequency, f, due to an interfering absorption, from said weighted magnitudes; and
   means for determining characteristics of said target gas, free of interferences by adjacent absorption lines, from the results of the calculation.

7. The improved system of claim 1 wherein said demodulator comprises a plurality of separate demodulators corresponding to selected frequency components.

8. The improved system of claim 7 wherein said plurality of separate demodulators each comprise:
   a local oscillator generating a frequency equal to a separate one of each of said selected frequency components output by said photodetector; and
   a mixer for performing homodyne demodulation of said frequency component.

9. The improved system of claim 7 wherein said plurality of separate demodulators each comprise:
   a local oscillator generating a frequency equal to a separate one of each of said selected frequency components output by said photodetector; and
   a lock-in amplifier for performing homodyne demodulation of said frequency component.

10. The improved system of claim 1 wherein said demodulator comprises:
   an analog-to-digital converter for converting the output of said photodetector into digital data; and a computer for performing numerical demodulation of said digital data.

11. The improved system of claim 10 further comprising a filter for filtering noise from the demodulated digital data.

12. The improved system of claim 10 wherein said computer comprises means for performing numerical demodulation via fast Fourier transforms.

13. The improved system of claim 10 wherein said computer comprises means for performing numerical demodulation via vector dot product operations.

14. In a wavelength modulation spectroscopy method comprising the steps of modulating at a frequency f and generating photodetector output with a plurality of frequency components at integer harmonics of said operating frequency f, an improvement comprising the step of demodulating a plurality of the frequency components of the photodetector output, including at least two even harmonics.

15. The improved method of claim 14 further comprising the step of extracting spectroscopic information from the demodulated frequency components to obtain absorption line shape information.

16. The improved method of claim 15 wherein the extracting spectroscopic information step comprises measuring line center magnitudes of selected even harmonics of the demodulated frequency components.

17. The improved method of claim 16 further comprising the step of calculating the absorption line shape from the relationship of the line center magnitudes.

18. The improved method of claim 14 further comprising the step of calculating at least one parameter from the group consisting of gas concentration, gas temperature, and gas pressure from spectroscopic information of the demodulated frequency components.

19. The improved method of claim 14 further comprising the steps of:
   a) constraining the mean modulation wavelength to the absorption line center of a target gas;
   b) measuring magnitudes of the demodulated frequency components;
   c) weighting magnitudes of selected odd harmonic demodulated frequency components based on known properties of a spectroscopic interference;
   d) calculating magnitudes of selected even harmonic demodulated frequency components due to an interfering absorption from the weighted magnitudes of the selected odd harmonic demodulated frequency components; and
   e) determining characteristics of the target gas, free of interferences by adjacent absorption lines, from the results of the calculation step.

20. The improved method of claim 14 wherein the demodulating step comprises demodulating selected frequency components with a plurality of separate demodulators corresponding to each of the selected frequency components.

21. The improved method of claim 20 wherein the demodulating selected frequency components step comprises:
   generating a frequency, equal to a separate one of each of the selected frequency components, with a local oscillator; and
   performing homodyne demodulation of each frequency component with a mixer.

22. The improved method of claim 20 wherein the demodulating selected frequency components step comprises:
   generating a frequency, equal to a separate one of each of the selected frequency components, with a local oscillator; and
   performing homodyne demodulation of each frequency component with a lock-in amplifier.

23. The improved method of claim 14 wherein the demodulating step comprises:
   converting the photodetector output into digital data with an analog-to-digital converter; and
   numerically demodulating the digital data with a computer.

24. The improved method of claim 23 further comprising the step of filtering noise from the demodulated digital data.

25. The improved method of claim 23 further comprising the step of numerically demodulating via fast Fourier transforms with a computer.

26. The improved method of claim 23 further comprising the step of numerically demodulating via vector dot product operations with a computer.

27. In a wavelength modulation spectroscopy system comprising modulation means operating at frequency f and a photodetector generating output with frequency components f, 2f, 3f, . . . , nf, where n is an integer greater than one, an improvement comprising a demodulator to demodulate a plurality of said frequency components output by said photodetector and further comprising means for extracting spectroscopic information from said demodulated frequency components to obtain absorption line shape information.

28. The improved system of claim 27 wherein said means for extracting spectroscopic information comprises means for measuring line center magnitudes of said demodulated frequency components demodulated at selected even harmonics of said operating frequency f.

29. The improved system of claim 28 further comprising means for calculating the absorption line shape from the relationship of said line center magnitudes.

30. The improved system of claim 27 wherein said system is constrained to the absorption line center of a target gas and wherein said system further comprises:
   means for measuring magnitudes of said demodulated frequency components;
   means for weighting said magnitudes of said demodulated frequency components demodulated at odd harmonics of said modulation frequency, f, based on known properties of a spectroscopic interference;
   means for calculating magnitudes of said frequency components at even harmonics of said modulation frequency, f, due to an interfering absorption, from said weighted magnitudes; and
   means for determining characteristics of said target gas, free of interferences by adjacent absorption lines, from the results of the calculation.

31. In a wavelength modulation spectroscopy method comprising the steps of modulating at a frequency f and generating photodetector output with frequency components f, 2f, 3f, . . . , nf, where n is an integer greater than one, an improvement comprising the steps of demodulating a plurality of the frequency components of the photodetector output and of extracting spectroscopic information from the demodulated frequency components to obtain absorption line shape information.

32. The improved method of claim 31 wherein the extracting spectroscopic information step comprises measuring line center magnitudes of selected even harmonics of the demodulated frequency components.

33. The improved method of claim 32 further comprising the step of calculating the absorption line shape from the relationship of the line center magnitudes.

34. The improved method of claim 31 further comprising the steps of:
  a) constraining the mean modulation wavelength to the absorption line center of a target gas;
  b) measuring magnitudes of the demodulated frequency components;
  c) weighting magnitudes of selected odd harmonic demodulated frequency components based on known properties of a spectroscopic interference;
  d) calculating magnitudes of selected even harmonic demodulated frequency components due to an interfering absorption from the weighted magnitudes of the selected odd harmonic demodulated frequency components; and
  e) determining characteristics of the target gas, free of interferences by adjacent absorption lines, from the result s of the calculation step.

* * * * *